US00PP34917P2

(12) United States Plant Patent
Krautmann

(10) Patent No.: US PP34,917 P2
(45) Date of Patent: Jan. 17, 2023

(54) ***MAGNOLIA* TREE NAMED 'MJK-MC1'**

(50) Latin Name: *Magnolia cylindrica*
Varietal Denomination: 'MJK-MC1'

(71) Applicant: Mark Edmund Krautmann, Salem, OR (US)

(72) Inventor: Mark Edmund Krautmann, Salem, OR (US)

( * ) Notice: Subject to any disclaimer, the term of this patent is extended or adjusted under 35 U.S.C. 154(b) by 25 days.

(21) Appl. No.: 17/875,337

(22) Filed: Jul. 27, 2022

(51) Int. Cl.
*A01H 6/00* (2018.01)
*A01H 5/00* (2018.01)

(52) U.S. Cl.
USPC ..... Plt./223

(58) Field of Classification Search
USPC ..... Plt./223
CPC ..... A01H 6/00; A01H 5/00
See application file for complete search history.

*Primary Examiner* — Keith O. Robinson
(74) *Attorney, Agent, or Firm* — C. Anne Whealy

(57) ABSTRACT

A new and distinct cultivar of *Magnolia* tree named 'MJK-MC1', characterized by its upright and columnar in overall tree form; moderately vigorous growth habit and moderate growth rate; relatively large caliper trunk; freely branching habit with numerous lateral branches providing a full and densely foliated appearance; sturdy, thick, leathery and durable green-colored leaves that resist biotic and abiotic damage; late bud break which reduces late frost damage to flowers and leaves; flowering on first year's growth; freely flowering habit with numerous large white and reddish purple-colored flowers; and good landscape performance and cold hardiness.

5 Drawing Sheets

Figure 1:
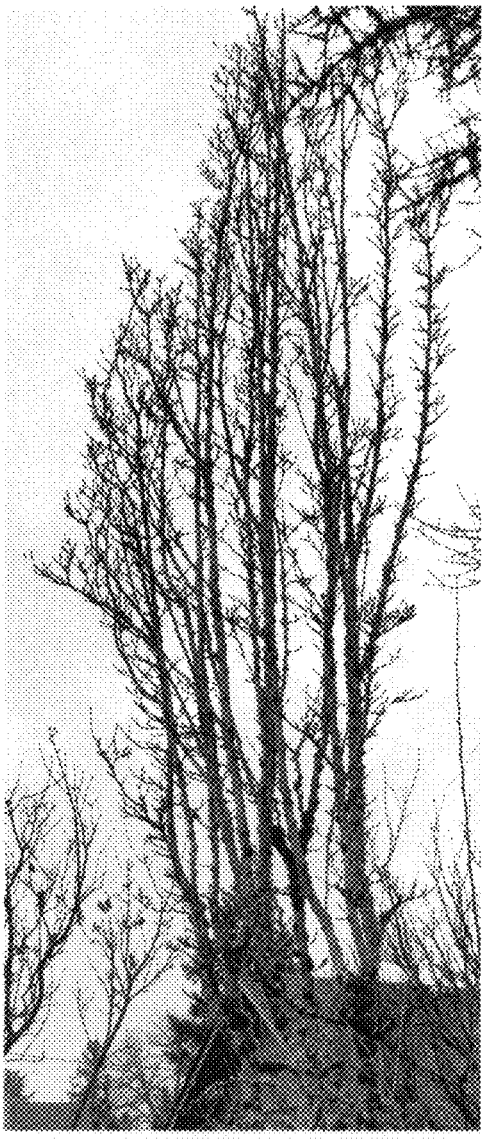

Botanical designation: *Magnolia cylindrica.*
Cultivar denomination: 'MJK-MC1'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of deciduous *Magnolia* tree, botanically known as *Magnolia cylindrica*, commercially referred to as the Huangshan *Magnolia* and hereinafter referred to by the name 'MJK-MC1'.

The new *Magnolia* tree originated from an open-pollination in Stayton, Oreg. in 1999 of an unnamed selection of *Magnolia cylindrica*, not patented, as the female, or seed, parent with an unknown selection of *Magnolia cylindrica* as the male, or pollen, parent. The new *Magnolia* tree was discovered and selected by the Inventor as a single plant from within the progeny of the stated open-pollination in a controlled environment in Stayton, Oreg. in July, 2002.

Asexual reproduction of the new *Magnolia* tree by grafting on *Magnolia kobus* rootstock in a controlled greenhouse environment in Stayton, Oreg. since May, 2015 has shown that the unique features of this new *Magnolia* tree are stable and reproduced true to type in successive generations.

SUMMARY OF THE INVENTION

Trees of the new *Magnolia* have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'MJK-MC1'. These characteristics in combination distinguish 'MJK-MC1' as a new and distinct *Magnolia* tree:

1. Upright and columnar in overall tree form; lateral branches relatively short and stout.
2. Moderately vigorous growth habit and moderate growth rate.
3. Relatively large caliper trunk.
4. Freely branching habit with numerous lateral branches providing a full and densely foliated appearance.
5. Sturdy, thick, leathery and durable green-colored leaves that resist biotic and abiotic damage.
6. Late bud break which reduces late frost damage to flowers and leaves.
7. Flowering on first year's growth.
8. Freely flowering habit with numerous large white and reddish purple-colored flowers.
9. Good landscape performance and cold hardiness.

Trees of the new *Magnolia* can be compared to trees of the female parent selection. Trees of the new *Magnolia* differ primarily from trees of the female parent selection in the following characteristics:

1. Trees of the new *Magnolia* are narrower and more columnar than trees of the female parent selection.
2. Trees of the new *Magnolia* flower on first year's growth whereas trees of the female parent selection do not start flowering until about seven years after propagation.
3. Trees of the new *Magnolia* are more freely flowering than trees of the female parent selection.
4. Trees of the new *Magnolia* are relatively more resistant to pathogens and pests common to *Magnolias* than trees of the female parent selection.

Trees of the new *Magnolia* can be compared to trees of *Magnolia* x *soulangiana* 'Galaxy', not patented. In side-by-side comparisons, trees of the new *Magnolia* and 'Galaxy' differ primarily in the following characteristics:

1. Trees of the new *Magnolia* are columnar and dense whereas trees of 'Galaxy' are more open and sparse.
2. Trees of the new *Magnolia* have strong and straight trunks whereas trees of 'Galaxy' have weak trunks and require staking to grow upright.
3. Bud break of trees of the new *Magnolia* is later than bud break of trees of 'Galaxy' which reduces late frost damage to flowers and leaves.
4. Flowers of trees of the new *Magnolia* are white and reddish purple in color whereas flowers of trees of 'Galaxy' are light lavender in color.
5. Trees of the new *Magnolia* are more resistant to pathogens and pests common to *Magnolias* than trees of 'Galaxy'.

BRIEF DESCRIPTION OF THE PHOTOGRAPHS

The accompanying colored photographs illustrate the overall appearance of the new *Magnolia* tree showing the colors as true as it is reasonably possible to obtain in colored reproductions of this type. Colors in the photographs may differ slightly from the color values cited in the detailed botanical description which accurately describe the colors of the new *Magnolia* tree grown in an outdoor nursery.

The photograph on the first sheet (FIG. 1) is a side perspective view of a typical mature tree of 'MJK-MC1' grown during the winter.

Figure 2:
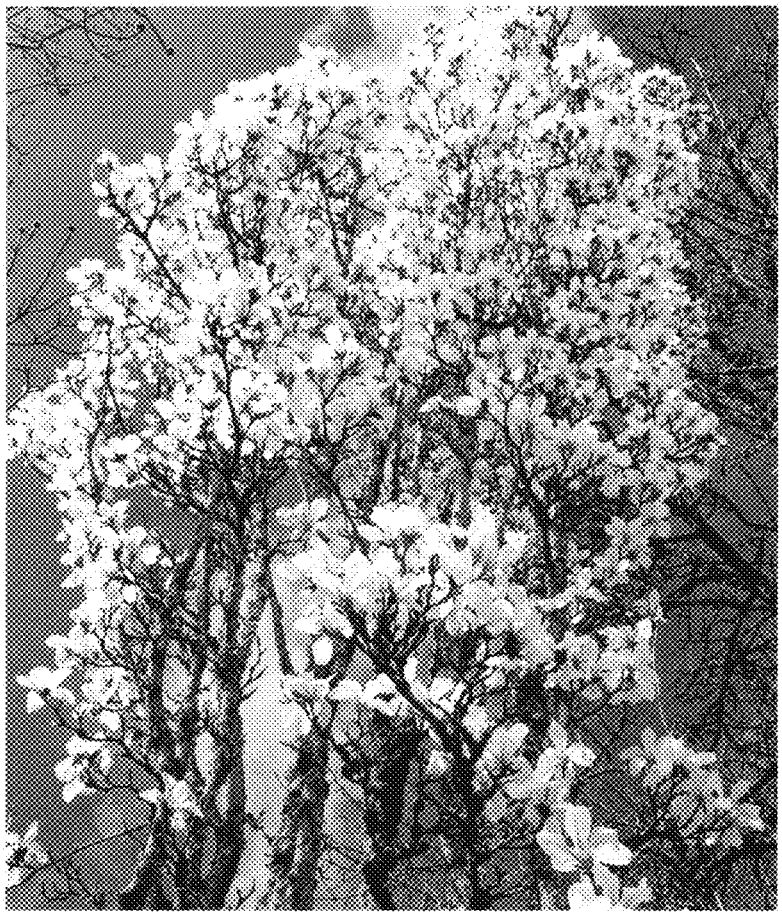

The photograph on the second sheet (FIG. 2) is a side perspective view of a typical flowering mature tree of 'MJK-MC1' grown during the spring.

Figure 3:
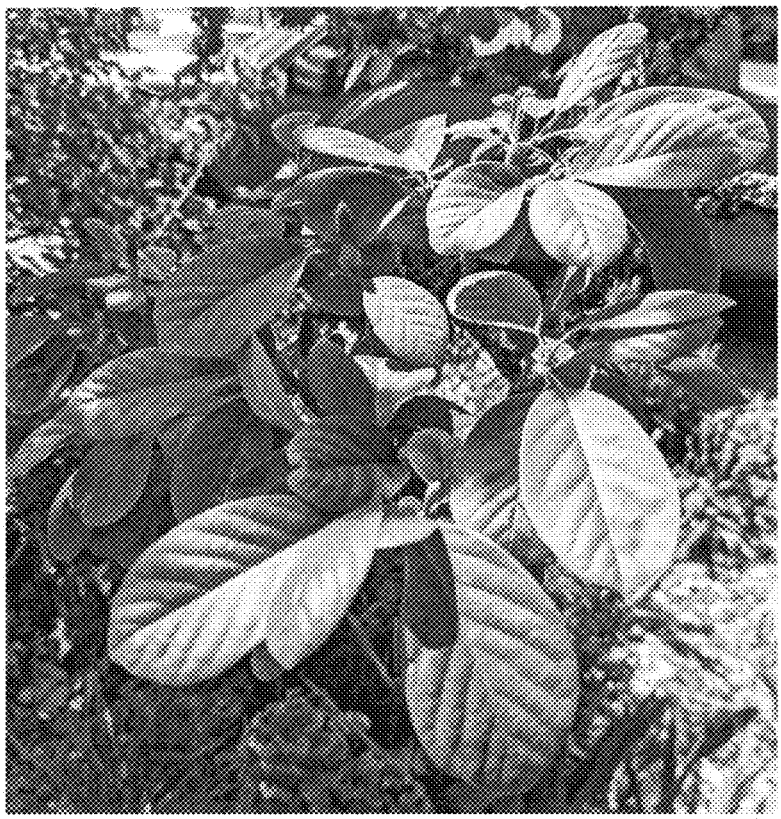

The photograph on the third sheet (FIG. 3) is a close up view of typical leaves of 'MJK-MC1'.

Figure 4:
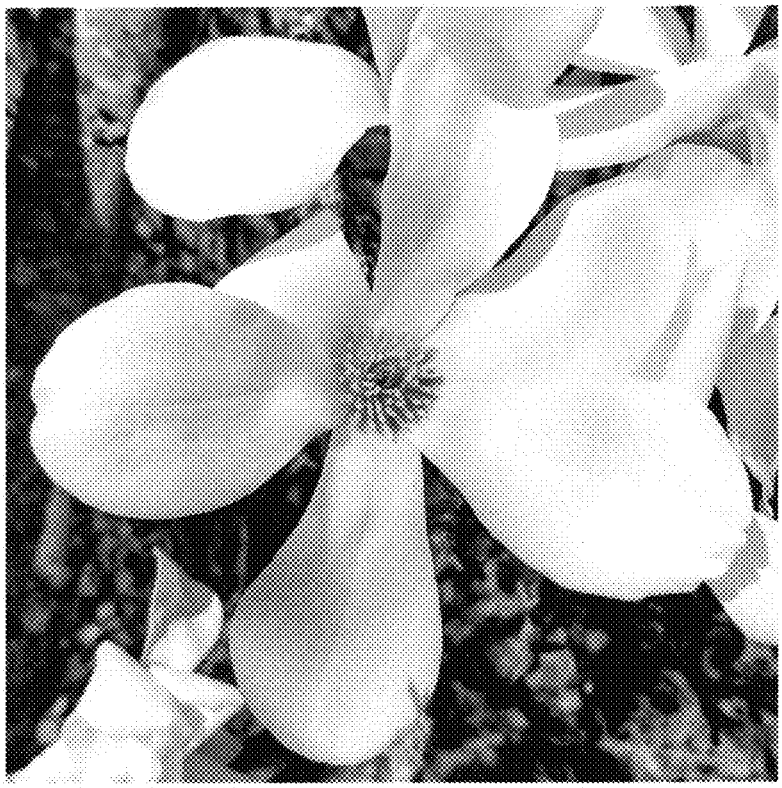

The photograph on the fourth sheet (FIG. 4) is a close-up view of typical flowers of 'MJK-MC1'.

Figure 5:
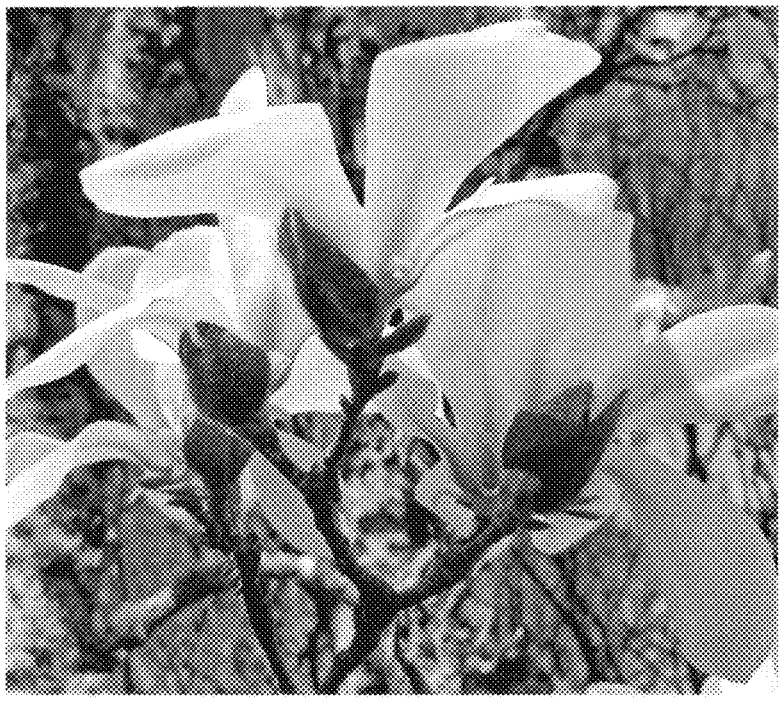

The photograph on the fifth sheet (FIG. 5) is side perspective views of typical flowers of 'MJK-MC1'.

DETAILED BOTANICAL DESCRIPTION

The aforementioned photographs and following observations, measurements and values describe trees grown during the late winter, spring and early summer in an outdoor nursery in Stayton, Oreg. and under cultural practices typical of commercial *Magnolia* tree production. Trees used in the photographs and description were ten years old. During the production of the trees, day temperatures ranged from about 4° C. to about 26° C. and night temperatures ranged from about −6° C. to about 13° C. In the following description, color references are made to The Royal Horticultural Society Colour Chart, 2007 Edition, except where general terms of ordinary dictionary significance are used.

Botanical classification: *Magnolia cylindrica* 'MJK-MC1'.

Parentage:

*Female, or seed, parent*.—Unnamed selection of *Magnolia cylindrica*, not patented.

*Male, or pollen, parent*.—Unknown selection of *Magnolia cylindrica*, not patented.

Propagation:

*Type*.—Plants of the new *Magnolia* tree are propagated in the early spring by grafting scions of the new *Magnolia* tree onto named or unnamed selections of *Magnolia kobus* rootstock.

Tree description:

*Tree form and growth habit*.—Deciduous flowering tree; upright and columnar in overall tree form; lateral branches relatively short and stout; moderately vigorous growth habit and moderate growth rate; relatively large caliper trunk; freely branching habit with numerous lateral branches providing a full and densely foliated appearance.

*Tree height*.—About 9.14 meters.

*Tree width* (*spread*).—About 1.83 meters.

*Trunk caliper*.—About 25 cm.

*Growth rate, height*.—About 70 to 100 cm per year.

*Number of lateral branches per tree*.—About 35 primary lateral branches each with about 20 secondary lateral branches.

*Branch length*.—About 91 cm to 122 cm.

*Branch diameter*.—About 2.5 cm to 3.8 cm.

*Branch internode length*.—About 12.7 cm to 15.2 cm.

*Branch angle orientation*.—Mostly upwardly, about 5° to 10° from vertical.

*Branch strength*.—Strong.

*Branch texture and luster*.—Smooth, glabrous; matte.

*Branch color*.—Close to 198D.

*Bark, mature and immature, texture and luster*.—Smooth, glabrous; matte.

*Bark, mature and immature, color*.—Close to 198D.

Leaf description:

*Arrangement*.—Alternate, simple.

*Length*.—About 8 cm.

*Width*.—About 5 cm.

*Shape*.—Elliptic to obovate.

*Apex*.—Acute.

*Base*.—Obtuse.

*Margins*.—Entire.

*Venation pattern*.—Pinnate.

*Texture and luster, upper and lower surfaces*.—Smooth, glabrous; coriaceous; matte.

*Color*.—When developing, upper and lower surfaces: Close to 146A. Fully developed, upper and lower surfaces: Close to 146A; venation, close to 146A; color becoming close to 200D in the autumn.

*Petioles*.—Length: About 1.5 cm. Diameter: About 2 mm. Strength: Moderately strong. Texture and luster, upper and lower surfaces: Smooth, glabrous; matte. Color, upper and lower surfaces: Close to 145B.

Flower description:

*Flower arrangement and habit*.—Large solitary flowers with numerous flowers developing per tree during the flowering season; flowers face mostly upright.

*Fragrance*.—None detected.

*Natural flowering season*.—Plants of the new *Magnolia* begin flowering in mid-March in Oregon.

*Flower longevity*.—Individual flowers last about seven to ten days on the plant; flowers not persistent.

*Flower diameter*.—About 10 cm.

*Flower length* (*depth*).—About 7 cm.

*Flower buds*.—Length: About 4.5 cm. Diameter: About 1.5 cm. Shape: Ovoid. Texture and luster: Pubescent; matte. Color: Close to 197B.

*Tepals*.—Quantity and arrangement: About six tepals arranged in a single whorl. Length: About 5.5 cm. Width: About 3.2 cm. Shape: Spatulate. Apex: Obtuse, occasionally retuse to emarginate. Base: Attenuate. Margin: Entire; not undulate. Texture and luster, upper and lower surfaces: Smooth, glabrous; coriaceous; matte. Luster, upper and lower surfaces: Matte. Color: When opening and fully opened, upper surface: Close to 155B; venation, close to 155B; color does not change with subsequent development. When opening and fully opened, lower surface: Close to 155B; proximal flare and towards the base, close to 58A; venation, close to 155B and 58A; color does not change with subsequent development.

*Sepals*.—Quantity and arrangement: About six sepals arranged in a single whorl. Length: About 4.5 cm. Width: About 1.5 cm. Shape: Ovate. Apex: Acute. Base: Obtuse. Margin: Entire. Texture and luster, upper surface: Smooth, glabrous; coriaceous; matte. Texture and luster, lower surface: Pubescent; coriaceous; matte. Color: When opening and fully opened, upper surface: Close to 197B. When opening and fully opened, lower surface: Close to 197B.

*Peduncles*.—Length: About 2.5 cm. Diameter: About 5 mm. Strength: Strong. Aspect: About 45° from stem axis. Texture and luster: Rough; matte. Color: Close to 198D.

*Reproductive organs*.—Stamens: Quantity: Numerous. Filament length: About 2 cm. Filament color: Close to 58A. Anther shape: Linear. Anther size: About 1 mm by 10 mm. Anther color: Close to 58A. Pollen amount: Scarce. Pollen color: Close to 22D. Pistils: Quantity per flower: One. Pistil length: About 1 cm. Style color: Close to 149D. Stigma diameter: About 2.5 mm. Stigma shape: Round. Stigma color: Close to 149D. Fruits: Fruit type: Follicetum. Quantity per plant: One fruit develops per flower. Length: About 6 cm. Diameter: About 2 cm. Shape: Cone-shaped. Texture and luster: Smooth, glabrous; matte. Color: Close to 59C and 142A. Seeds: Quantity per fruit: About 80. Length: About 1 cm. Diameter: About 1 cm. Shape: Disc-shaped. Texture and luster: Smooth, glabrous; matte. Color: Close to 199B.

Temperature tolerance: Trees of the new *Magnolia* have been observed to have superior cold and heat tolerance and tolerate temperatures ranging from −25° C. to 45° C. and to be suitable for USDA Hardiness Zones 5 to 8.

Pathogen & pest tolerance: Trees of the new *Magnolia* have been observed to be resistant to Powdery Mildew (*Erysiphe* spp.) and Leaf Spot (*Rhynchosporium* spp., *Dreschlera* spp. and *Bipolaris* spp.) Additionally, trees of the new *Magnolia* have been observed to be resistant to spider mites (*Oligonychus ununguis* and *Tetranycus urticae*) and snails (*Helix* spp.). To date, trees of the new *Magnolia* have been not been observed to be tolerant to other pathogens and pests common to *Magnolia* trees.

It is claimed:

1. A new and distinct *Magnolia* tree named 'MJK-MC1' as illustrated and described.

* * * * *